(12) United States Patent
Simmet et al.

(10) Patent No.: US 6,174,876 B1
(45) Date of Patent: Jan. 16, 2001

(54) USE OF BOSWELLIC ACID FOR TREATING BRAIN TUMORS

(75) Inventors: Thomas Simmet, Bochum; Hermann P. T. Ammon, Tübingen, both of (DE)

(73) Assignee: Thomas Simmet, Bochum (DE)

( * ) Notice: Under 35 U.S.C. 154(b), the term of this patent shall be extended for 0 days.

(21) Appl. No.: 09/348,118

(22) Filed: Jul. 2, 1999

Related U.S. Application Data

(63) Continuation of application No. PCT/EP95/05073, filed on Dec. 21, 1995, which is a continuation of application No. 08/849,542, filed on Jun. 10, 1997, now Pat. No. 5,919,821.

(30) Foreign Application Priority Data

Dec. 21, 1994 (DE) ................................................ 44 45 728

(51) Int. Cl.$^7$ .................................................... A61K 31/43
(52) U.S. Cl. .......................... 514/198; 518/510; 518/554; 518/170; 518/171
(58) Field of Search .................................... 514/198, 170, 514/171, 510, 554

(56) References Cited

U.S. PATENT DOCUMENTS 5,064,823   11/1991   Lee et al. ............................. 514/198

FOREIGN PATENT DOCUMENTS

WO 90/01937   3/1990   (WO) .

OTHER PUBLICATIONS

Glenn J. Lesser and Stuart Grossman, "The Chemotherapy of High–Grade Astrocytomas", *Seminars in Oncology*, 21220–235 (Apr. 1994).

De Vita, D., Helman, S. Rosenberg, S.A. (eds.), *Cancer—Principles and Practice of Oncology*, 4th Edition, 1993, pp. 1695–1737, J.B. Lippincott Company, Philadelphia, PA.

*Primary Examiner*—Frederick Krass
(74) *Attorney, Agent, or Firm*—Akin, Bump, Strauss, Hauer & Feld, L.L.P.

(57) ABSTRACT

The present invention relates to the use of pure boswellic acid, a physiologically acceptable salt, a derivative, a salt of said derivative or a vegetable preparation containing boswellic acid for the preparation of a pharmaceutical composition for the treatment of brain tumours.

13 Claims, No Drawings

USE OF BOSWELLIC ACID FOR TREATING BRAIN TUMORS

CROSS-REFERENCE TO RELATED APPLICATION

This application is a division of U.S. patent application Ser. No. 08/849,542, filed Jun. 10, 1997 and now U.S. Pat. No. 5,919,821, which in turn was an application filed under 35 U.S.C. § 371 of PCT/EP95/05073, having an international filing date of Dec. 21, 1995.

BACKGROUND OF THE INVENTION

The present invention relates to the use of pure boswellic acid, a physiologically acceptable salt, a derivative, a salt of said derivative or a vegetable preparation containing boswellic acid for the production of a pharmaceutical composition for the treatment of brain tumours.

The present invention also relates to the use of pure boswellic acid, a physiologically acceptable salt, a derivative, a salt of said derivative or a vegetable preparation containing boswellic acid for the treatment of brain tumours.

The possibilities known to date for the therapeutical treatment of brain tumours are unsatisfactory:

So far, the possibilities for a treatment of malignant brain tumours are insufficient. Neurosurgical removal of the brain tumours represents severe surgery and, depending on type, size and position of the brain tumours, in many cases does not lead to the complete removal of the malignant tumours. For these reasons, the average survival of the patients suffering from malignant brain tumours is only about 9 months even after a combined treatment including surgery and radiotherapy. An additional chemotherapy using the cytostatics known so far is able to achieve a prolongation of the survival of only about 10% (Lesser, G. J., Grossman S., The chemotherapy of high-grade astrocytomas, Seminars in Oncology, 1994, 21:220–235).

Glucocorticosteroids have been used for the symptomatic treatment which, however. are not able to effectively reduce the peritumoural brain oedemas so that their use does achieve the desired success.

Therefore, it is an object of the present invention to provide the use of preparations useful for the treatment of brain tumours, the inhibition of the peritumoural brain oedema as well as the growth of tumour cells, and for the destruction of the tumour cells. In particular. there is provided a preparation which, without exhibiting the side effects and the reduced efficiency accompanying the use of the cytostatics employed to date for the therapy of tumours, allow a significantly more efficient treatment of brain tumours. The pharmaceutical composition or preparation, respectively, provided according to the invention is intended to show a lower toxicity and, therefore, to be well tolerated by the patients. Much research has been carried out to provide a pharmaceutical composition of that type (De Vita, D., Helman, S., Rosenberg, S. A. (eds.), Cancer—Principles and Practice of Oncology, 4th edition, 1993, J. B. Lippincott Company, Philadelphia; Lesser, G. J., Grossman, S., The chemotherapy of high-grade astrocytomas, Seminars in Oncology, 1994, 21:220–235), documenting the high demand for the creation of such a pharmaceutical composition.

Now, it has been surprisingly found that boswellic acid, a physiologically acceptable salt, a derivative, a salt of said derivative or a vegetable preparation containing boswellic acid is effective for the treatment of brain tumours.

India's ayurvedic medicine uses pharmaceutical compositions containing preparations from the plant *Boswellia serrata* for the treatment of inflammation but also of rheumatism. However, there are no publications containing evidence as to the treatment of brain tumours using these pharmaceutical compositions. Due to the efficacy of preparations from the plant *Boswellia serrata* in the treatment of inflammable diseases this gum has already been examined with respect to its components. Thus, Pardhy & Bhattacharyya report (Ind. J. Chem., 16B:176–178, 1978) that *Boswellia serrata* contains essentially the following components:

βboswellic acid, acetyl-β-boswellic acid, acetyl-11-keto-β-boswellic acid, 11-keto-β-boswellic acid.

SUMMARY OF THE INVENTION

So far, no research is known concerning the efficacy of these compounds for the treatment of brain tumours.

In the following, the structural formulas of boswellic acid and some of its derivatives are shown:

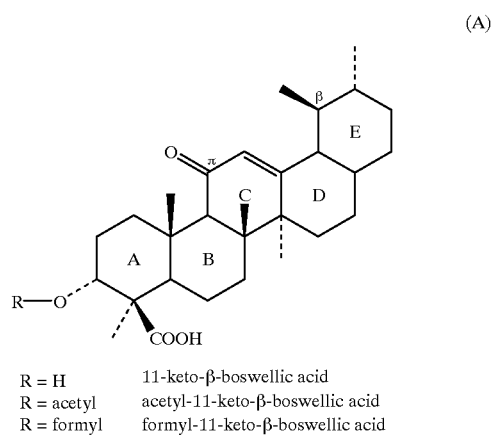

(A)

R = H      11-keto-β-boswellic acid
R = acetyl      acetyl-11-keto-β-boswellic acid
R = formyl      formyl-11-keto-β-boswellic acid

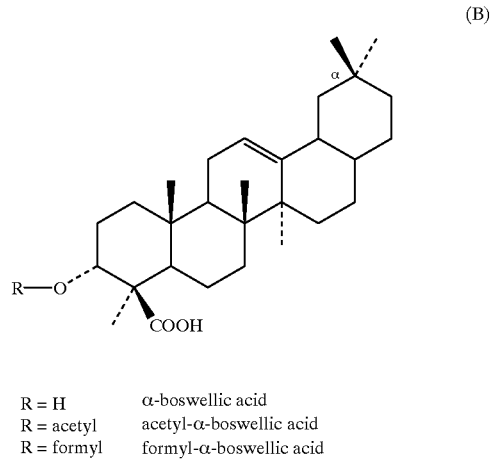

(B)

R = H      α-boswellic acid
R = acetyl      acetyl-α-boswellic acid
R = formyl      formyl-α-boswellic acid As boswellic acid, there is preferably used β-boswellic acid which according to references has been isolated from *Boswellia serrata* or other known plants containing boswellic acid. The β-boswellic acid may contain, in minor amounts α- or β-boswellic acid. As physiologically acceptable salts of boswellic acid, there may be used the sodium, potassium, ammonium, calcium salts. As derivatives of boswellic acid, there may be used lower alkyl esters obtained by esterification of the carboxyl group with an $C_1$–$C_6$ alcohol, preferably the methyl ester, or esters obtained by esterification of the hydroxyl group with a physiologically acceptable carboxylic acid. Preferred derivatives are β-boswellic acetate, β-boswellic formate, β-boswellic acid methyl ester, acetyl-β-boswellic acid, acetyl-11-keto-β-boswellic acid, and 11-keto-β-boswellic acid.

DETAILED DESCRIPTION OF THE INVENTION

Further, according to the invention it is possible to use a vegetable preparation containing boswellic acid. According to the invention, there are used preparations obtained from the gum of Boswellia species (olibanum, incense).

Plants containing boswellic acid (syn.: boswellinic acid) are:

Boswellia (serrata, papyrifera, frereana, carteri, thurifera, glabra, bhaw-dajiana, oblongata, socotrana and other members of this family).

An ethanolic extract from the gum of Boswellia serrata containing the above mentioned boswellic acids proves to be especially efficient: the application of this preparation—in the following referred to as phytopharmacon H 15 (produced and sold by the company Ayurmedica, Pöcking)—allows within a treatment period of seven days to achieve a reduction of the peritumoural brain oedema of 22 to 48%. A histopathological examination of the tumour tissue of the patients treated shows to be necrotic as far as possible, a fact that is extraordinarily exceptional. The vitality of the explanted cells is extraordinarily low and is about 3.5 to 4.5% in cell cultures. Usually, the vitality of such cells is about 80%. In contrast to the cells of untreated patients, the cells of the treated tumour tissue show no tendency to proliferate within two weeks.

These experiments show that H 15 inhibits the peritumoural brain oedema as well as tumour growth and leads to the death of the tumour cells.

Further, according to the invention there is the possibility that the use is carried out together with other chemically pure pharmaceutical agents and/or other vegetable drugs. Examples for such other chemically pure pharmaceutical agents are the following:

Cytostatics, e.g. nimustine, carmustine, lomustine, methyl lomustine, semustine, methotrexate, teniposide, dacarbacine, procarbacine, temozolamide, topotecane, paclitaxel. streptococine, cisplatin, 5-fluoro uracil; glucocorticosteroids, such as dexamethasone, prednisolone, methyl prednisolone, prednisone, hydrocortisol, cloprednole, betamethasone.

An example for such a vegetable drug is vincristine.

According to the invention, the boswellic acid is administered as required. Since it has a low toxicity, the dosage is not critical and can be easily varied by the physician depending on the severity of the disease, the weight of the patient to be treated and the duration of the treatment.

For example, unit dosages may be administered once to four times per day. The exact dose depends on the route of administration and the condition to be treated. Naturally, it can be required to carry out routine variations of the dose depending on the age and weight of the patient as well as the severity of the disease state.

The preparations used according to the invention can be formulated in a manner known per se using one or more of pharmaceutically acceptable carriers or diluents. The preparations can be formulated for oral, parenteral, rectal, intracranial or intrathecal administration. Preparations of the compounds for oral administration are preferred.

The pharmaceutical preparations for oral administration may be in the form of tablets or capsules prepared according to procedures known per se together with pharmaceutically acceptable diluents, such as binding agents (for example pregelatinated corn starch, polyvinylpyrrolidone or hydroxypropylmethyl cellulose), fillers (for example lactose, sucrose, mannitol, corn starch, microcristalline cellulose or calcium hydrogen phosphate); lubricants (for example stearic acid: polyethylenglycol, magnesium stearate, talc or silica); desintegration agents (for example potato starch, sodium starch glycolate or sodium carboxymethylcellulose); or wetting agents (for example sodium lauryl sulfate). The tablets may be coated according to known procedures. Liquid preparations for oral administration can be for example in the form of aqueous or oily solutions, syrups, elixirs, emulsions or suspensions, or can be in the form of a dry product for the reconstitution with water or another suitable carrier prior to use. Such liquid preparations can be prepared according to procedures known per se with pharmaceutically acceptable additives, such as suspension agents (for example sorbitic syrup, cellulose derivatives, glucose/sugar syrup, gelatin, aluminiun stearate gel or hydrogenated edible fats); emulsifying agents (for example lecithin, arabic gum or sorbitan monooleate); non-aqueous carriers (for example mandelic oil, oily esters, ethyl alcohol or fractionated vegetable oils); and preservatives (for example methyl or propyl-p-hydroxy-benzoates or sorbic acid). The liquid preparations can also contain buffers, flavouring agents, colouring agents, and sweetening agents known per se as required.

For parenteral administration the compounds may be formulated for injection. preferably intravenous, intraarterial, intramuscular, intracranial, intrathecal or subcutaneous injections. Preparations for injection can be in unit dosage form, e.g. in ampoules, or in multiple dose containers with a preservative added. The preparations may be in the form of suspensions, solutions, or emulsions in oily or aqueous carriers, and may contain preparation additives such as suspending, stabilizing and/or dispersing agents, and/or agents for adjusting the tonicity of the solution. Alternatively, the active ingredient can be in powder form for reconstitution with a suitable carrier, for example sterile pyrogen-free water prior to use.

The compounds may also be formulated as rectal preparations such as suppositories, for example of the kind containing suppository bases known per se, such as cocoa butter or other glycerides.

The following Examples illustrate the use according to the invention.

EXAMPLE 1

Tablets for oral administration

A. Direct compression (1)

| | | |
|---|---|---|
| Active agent: | boswellic acid | 15–30 mg/tablet |
| (or pulverized drug, respectively, | | 0.5–1.0 g/tablet) |
| Magnesium stearate BP | | 0.65 mg/tablet |
| Dry lactose | | 80 mg/tablet |

The active agent is compounded together with the dry lactose, and the mixture is screened. The obtained mixture is compressed to form tablets using a tablet-compressing machine.

(2)

| | | |
|---|---|---|
| Active agent: | boswellic acid | 15–30 mg/tablet |
| (or pulverized drug, respectively, | | 0.5–1.0 g/tablet) |
| Magnesium stearate BP | | 0.7 mg/tablet |
| Microcristalline cellulose NF | | 100 mg/tablet |

The active agent is screened and is compounded with the microcristalline cellulose and magnesium stearate. The obtained mixture is compressed to form tablets using a tablet-compressing machine.

| B. Wet granulation | | |
|---|---|---|
| Active agent: | boswellic acid | 15–30 mg/tablet |
| (or pulverized drug, respectively, | | 0.5–1.0 g/tablet) |
| Lactose BP | | 150.0 mg/tablet |
| Starch BP | | 30.0 mg/tablet |
| Pregelatinated corn starch BP | | 15.0 mg/tablet |
| Magnesium stearate BP | | 1.5 mg/tablet |

The active agent is screened by a suitable sieve and is compounded with lactose, starch and the pregelatinated corn starch. Suitable volumina of pure water are added, and the powder is granulated. After drying, the granulate is sieved and mixed with the magnesium stearate. Then, the granulate is compressed to form tablets by using a punch having a suitable diameter.

Tablets having a different composition can be produced by varying the ratio of active agent to lactose or the weight of compression, and using a suitable punch.

EXAMPLE 2

| Capsules | | |
|---|---|---|
| Active agent: | boswellic acid | 15–30 mg/capsule |
| (or granulated drug, respectively, | | 0.5–1.0 g/capsule) |
| Free-flowing starch | | 150.00 mg/capsule |
| Magnesium stearate BP | | 1.00 mg/capsule |

The active agent is screened and mixed with the other components. The mixture is filled into hard gelatin capsules No. 2 using a suitable apparatus. Other capsules can be prepared by varying the filling weight, and, if required, varying the size of the capsule.

EXAMPLE 3

| Syrup | | |
|---|---|---|
| Sucrose-free preparation | | mg/5 ml dose |
| Active agent: | boswellic acid | 15–30 |
| Hydroxy propyl methyl cellulose USP | | |
| (Viscosity type 4000) | | 22.5 |
| Buffer | ) | |
| Flavouring agent | ) | |
| Colouring agent | ) | as required |
| Preservative | ) | |
| Sweetening agent | ) | |

-continued

| Syrup | | |
|---|---|---|
| Sucrose-free preparation | | mg/5 ml dose |
| Pure water | Q.s. to | 5.0 ml |

The hydroxypropyl methyl cellulose is dispersed in pure water, cooled and afterwards mixed with an aqueous suspension containing the active agent and the other components of the preparation. The solution obtained is adjusted to its volume and mixed.

EXAMPLE 4

| Suspension | | mg/5 ml dose |
|---|---|---|
| Active agent: | boswellic acid | 15–30 |
| (or pulverized drug, respectively, | | 0.5–1.0 g) |
| (or appropriate amount of dried drug extract) | | |
| Aluminium monostearate | | 75.00 |
| Sweetening agent | ) | |
| Flavouring agent | ) | as required |
| Colouring agent | ) | |
| Fractionated coconut oil | Q.s. to | 5.00 |

The aluminium monostearate is dispersed in approximately 90% of fractionated coconut oil. The resulting suspension is heated to 115° C. under stirring, followed by cooling. The—sweetening, flavouring and colouring agents are added, and the active agent is dispersed. The suspension then is adjusted to volume with the remaining fractionated coconut oil and mixed.

EXAMPLE 5

| Sublingual tablet | | |
|---|---|---|
| Active agent: | boswellic acid | 15–30 mg/tablet |
| (or drug extract, respectively, | | 0.5–1.0 g/tablet) |
| Compressable sugar NF | | 50.5 mg/tablet |
| Magnesium stearate BP | | 0.5 mg/tablet |

The active agent is screened by passage through a suitable sieve, compounded with the other components and compressed using suitable punches. Tablets of different strength can be prepared by varying the active agent to carrier ratio or the compressing weight.

EXAMPLE 6

| Suppositories for rectal administration | | |
|---|---|---|
| Active agent: | boswellic acid | 15–30 mg |
| Witepsol H15[+] | Q.s. to | 1.0 g |

[+]suitable quality of Adeps solidus Ph. Eur.

A suspension is made of the active agent in molten Witepsol and is filled into suppository forms of 1 g using a suitable apparatus.

EXAMPLE 7

| Injection for intravenous administration | | |
|---|---|---|
| Active agent: | boswellic acid | 15–30 mg/ml |
| Sodium chloride intravenous infusion, BP, 0.9 wt. %/vol. | Q.s. to | 1 ml |
| Batch size | 2500 ml | |

The active agent is dissolved in a portion of the sodium chloride intravenous infusion, the solution is adjusted to volume using sodium chloride intravenous infusion, and the solution is thoroughly mixed. The solution is filled into clear 10 ml glass ampoules type 1 and is head space sealed under nitrogen by melting off the glass. The ampoules are sterilized by heating in an autoclave at 120° C. for not less than 20 minutes.

What is claimed is:

1. A method of treating a patient having a brain tumor and a peritumoral brain edema, the method comprising administering to the patient a pharmaceutical composition comprising at least one component selected from the group consisting of pure boswellic acid, 11-keto-β-boswellic acid, a lower alkyl ester of pure boswellic acid, a lower alkyl ester of 11-keto-β-boswellic acid, wherein the ester is obtained by at least one of esterification of the carboxyl group with a $C_1$–$C_6$ alcohol and by esterification of the hydroxyl group by a physiologically acceptable carboxylic acid, and a physiologically acceptable salt of any of them, the component being present in an amount effective to treat the brain tumor and treat the peritumoral brain edema.

2. The method of claim 1, wherein the pharmaceutical composition is administered to inhibit peritumoral brain edema and growth of tumor cells as well as for destroying tumor cells.

3. The method of claim 1 wherein the peritumoral brain edema is reduced.

4. The method of claim 1, wherein the pharmaceutical composition is administered by a route selected from the group consisting of an oral, buccal, rectal, intramuscular, subcutaneous, intraarticular, intravenous, intracranial, and intrathecal administration route.

5. The method of claim 1, wherein the pharmaceutical composition is in a form selected from the group consisting of tablets, dragees, capsules, solutions, polymerbound preparations, and suppositories.

6. The method of claim 1 wherein the physiologically acceptable carboxylic acid is acetic acid or formic acid.

7. The method of claim 1 wherein the composition comprises at least one component selected from the group consisting of β-boswellic acid, acetyl-β-boswellic acid, acetyl-11-keto-β-boswellic acid, 11-keto-β-boswellic acid, formyl-11-keto-β-boswellic acid, α-boswellic acid, acetyl-α-boswellic acid, formyl-α-boswellic acid, β-boswellic acetate, β-boswellic formate, β-boswellic acid methyl ester, and a salt of any of them selected from the group consisting of a sodium salt, a potassium salt, an ammonium salt and a calcium salt thereof.

8. The method of claim 1 further comprising also administering with the composition a pharmaceutical agent selected from the group consisting of a chemically pure drug and a vegetable drug.

9. The method of claim 8 wherein the chemically pure drug is a cytostatic drug.

10. The method of claim 9 wherein the cytostatic drug is selected from the group consisting of nimustine, carmustine, lomustine, methyl lomustine, semustine, methotrexate, teniposide, dacarbacine, procarbacine, temozolamide, topotecane, paclitaxel, streptococine, cisplatin and 5-fluoro uracil.

11. The method of claim 8 wherein the chemically pure drug is a glucocorticosteroid.

12. The method of claim 11 wherein the glucocorticosteroid is selected from the group consisting of dexamethasone, prednisolone, methyl prednisolone, prednisone, hydrocortisol, cloprednole and betamethasone.

13. The method of claim 8 wherein the vegetable drug is vincristine.

* * * * *